(12) United States Patent
Lowe et al.

(10) Patent No.: US 6,231,514 B1
(45) Date of Patent: *May 15, 2001

(54) DEVICE FOR USE IN TEMPORARY INSERTION OF A SENSOR WITHIN A PATIENT'S BODY

(75) Inventors: Robert I. Lowe; Anthony P. Furnary, both of Portland, OR (US)

(73) Assignee: Tobo, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/274,150

(22) Filed: Mar. 22, 1999

Related U.S. Application Data

(63) Continuation-in-part of application No. 09/046,369, filed on Mar. 23, 1998, which is a continuation-in-part of application No. 08/672,484, filed on Jun. 26, 1996, now Pat. No. 5,775,328.

(51) Int. Cl.[7] .......................................... A61B 8/14
(52) U.S. Cl. ............................................. 600/462
(58) Field of Search ..................... 600/459, 462, 600/466, 467, 468, 481, 483; 604/27; 607/9, 122, 123, 124

(56) References Cited

U.S. PATENT DOCUMENTS

| | | | |
|---|---|---|---|
| 3,878,849 | 4/1975 | Muller et al. | 128/349 |
| 4,100,309 | 7/1978 | Micklus et al. | 427/2 |
| 4,407,294 | 10/1983 | Vilkomerson | 128/660 |
| 4,408,612 | 10/1983 | Utsugi | 128/660 |
| 4,428,379 | 1/1984 | Robbins et al. | 128/660 |
| 4,431,006 | 2/1984 | Trimmer et al. | 128/660 |
| 4,671,295 | 6/1987 | Abrams et al. | 128/663 |
| 4,722,347 | 2/1988 | Abrams et al. | 128/663 |
| 4,867,141 | 9/1989 | Nakada et al. | 128/24 |

(List continued on next page.)

FOREIGN PATENT DOCUMENTS

| | | | |
|---|---|---|---|
| 2 268 074 | 1/1994 | (GB) | A61M/25/04 |
| WO 93/03668 | 3/1993 | (WO) | A61B/5/029 |

*Primary Examiner*—George Manuel
(74) *Attorney, Agent, or Firm*—Chernoff, Vilhauer, McClung & Stenzel, LLP

(57) ABSTRACT

A device for use in placing a non-sterile sensor probe (70, 154, 180, 206, 208) such as an ultrasound scanning transducer in a desired position within a patient's body (12), with a probe-receiving tube (36, 92, 143, 139, 152, 201, 203, 205) having a closed distal end (38, 95, 212, 220, 222) so that a probe inserted within the tube through an open proximal end (49, 97) located outside the patient's body is isolated from contact with or contamination of the interior of the patient's body. The probe-receiving tube is attached to and extends alongside an elongate support member (18, 82, 130, 134, 138, 142, 200, 202, 204) which aids in placement of the probe-receiving tube in a location proximate an organ to be observed by use of a sensor probe in the probe-receiving tube. The elongate support member may be a chest drain tube. Further, the device may have one or more of the following features: integrated fastening mechanisms (66, 132, 136, 140) suitable to anchor the device within the patient's body; an attached sterile sensor (141) that may be attached directly to an interior blood vessel (147); an attached pair of sterile temporary pacing wires (151*a*, 151*b*) that may be attached directly to a heart; a flexible extension sleeve (150) attached to the probe-receiving tube; at least one hydrostatic valve (75) positioned within the probe-receiving tube or the extension sleeve; and alternate sensors (180) such as an ultrasonic sensor, a light emitting sensor, or a multi-function combination sensor may be used in the probe-receiving tube. The device may also be a guidable surgical device such as a forward-looking guidable trocar (200), a laterally-looking guidable trocar (202), or a guidable biopsy needle (204) that have a probe-receiving tube (201, 203, 205) defined longitudinally therein that is suitable for receiving a sensor probe used for guiding the guidable device.

40 Claims, 9 Drawing Sheets

U.S. PATENT DOCUMENTS

| | | | |
|---|---|---|---|
| 4,886,059 | 12/1989 | Weber | 128/207.15 |
| 4,947,854 | 8/1990 | Rabinovitz et al. | 128/662.04 |
| 5,048,524 | 9/1991 | Bailey | 128/634 |
| 5,095,910 | 3/1992 | Powers | 128/662 |
| 5,127,407 | 7/1992 | Tan | 128/633 |
| 5,205,292 | 4/1993 | Czar et al. | 128/662.03 |
| 5,228,440 | 7/1993 | Chung et al. | 128/633 |
| 5,265,612 | 11/1993 | Sarvazyan et al. | 128/660.01 |
| 5,284,146 | 2/1994 | Czar et al. | 128/662.03 |
| 5,291,896 | 3/1994 | Fonger et al. | 128/713 |
| 5,304,214 | 4/1994 | DeFord et al. | 607/105 |
| 5,315,995 | 5/1994 | Rivers | 128/634 |
| 5,331,947 | 7/1994 | Shturman | 126/4 |
| 5,335,663 | 8/1994 | Oakley et al. | 128/662 |
| 5,443,445 | 8/1995 | Peters et al. | 604/27 |
| 5,531,714 | 7/1996 | Dahn et al. | 604/264 |
| 5,673,694 | 10/1997 | Rivers | 128/634 |
| 5,743,260 | 4/1998 | Chung et al. | 128/633 |
| 5,743,261 | 4/1998 | Mainiero et al. | 128/633 |
| 5,775,328 | 7/1998 | Lowe et al. | 128/662.06 |

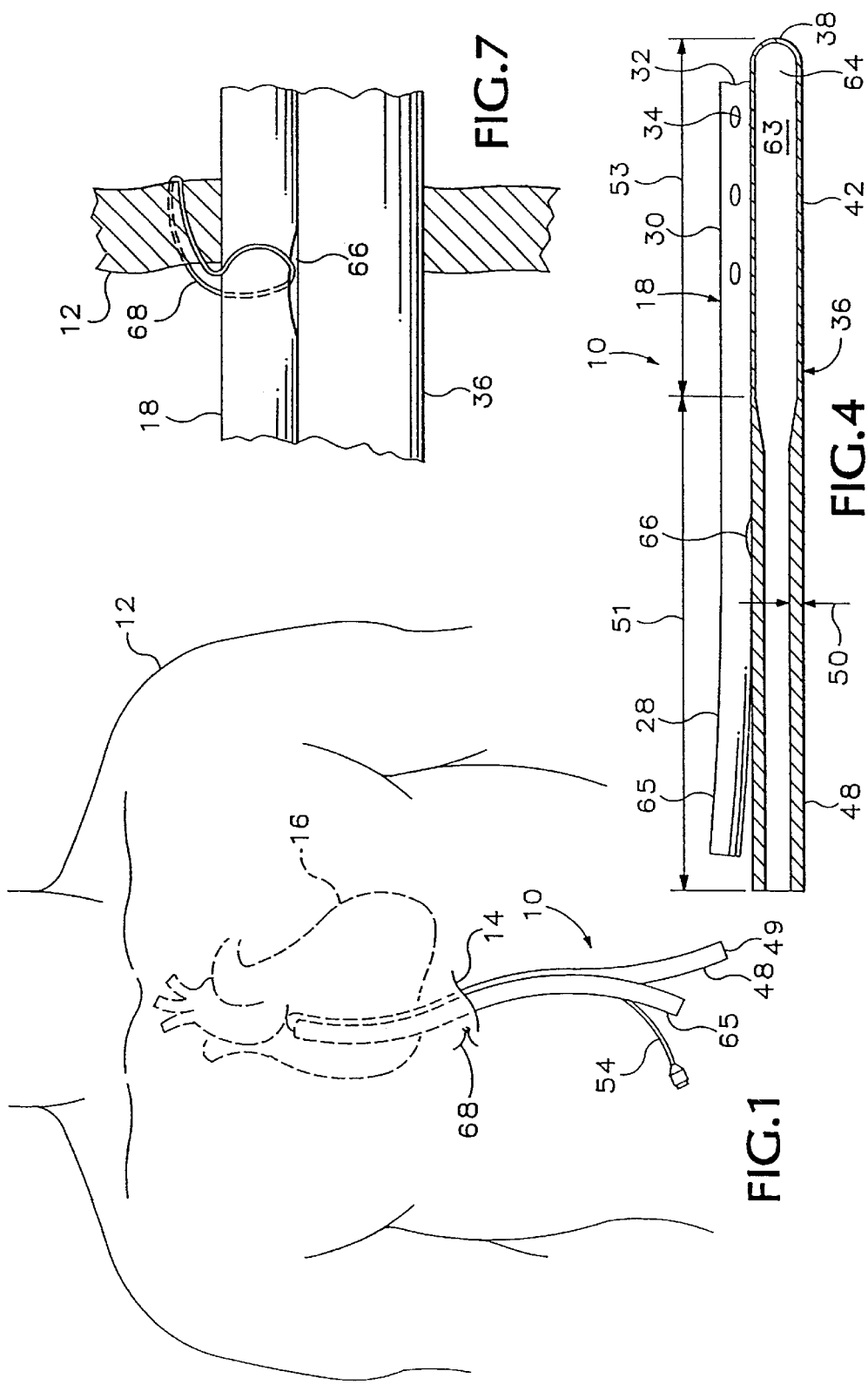

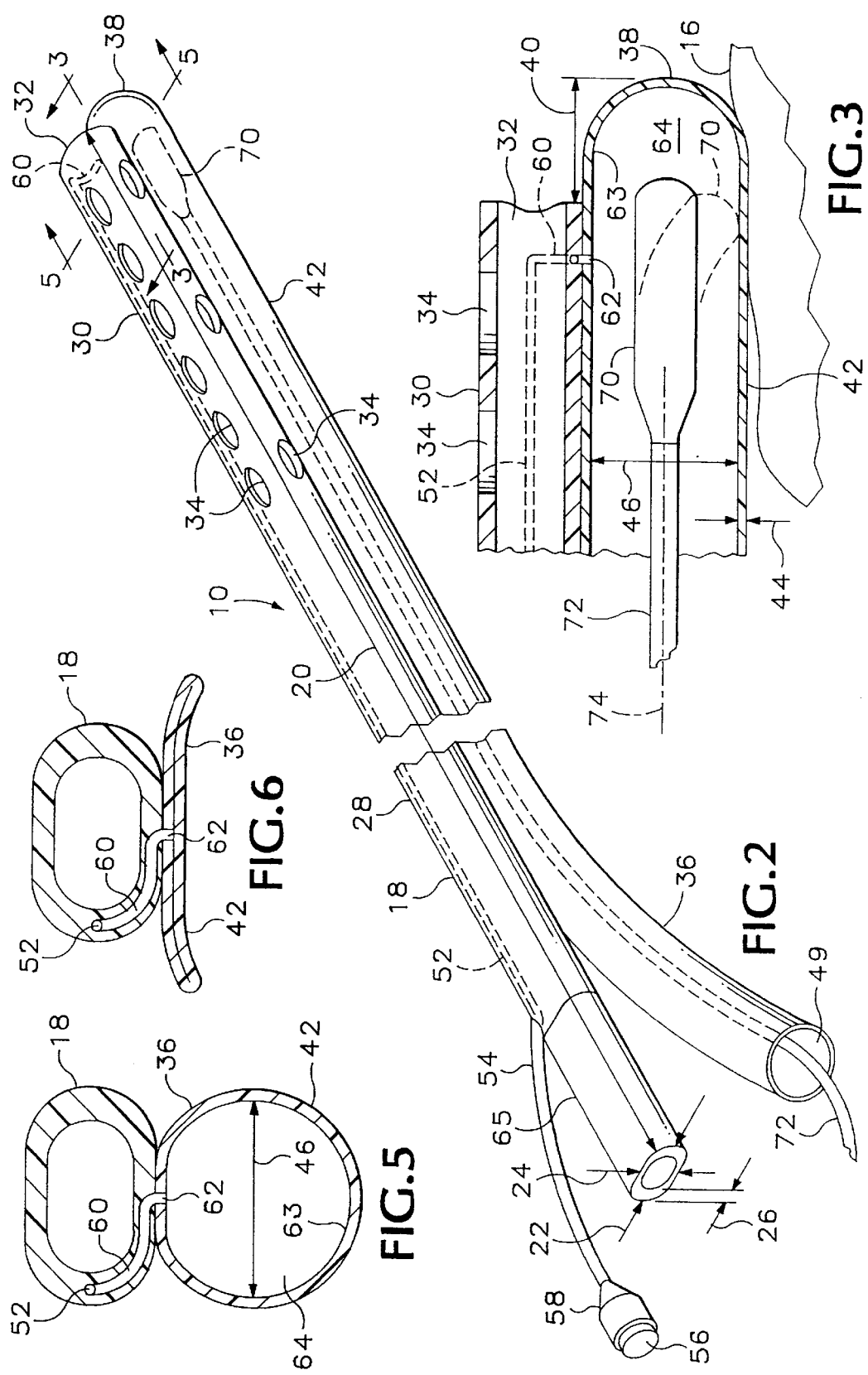

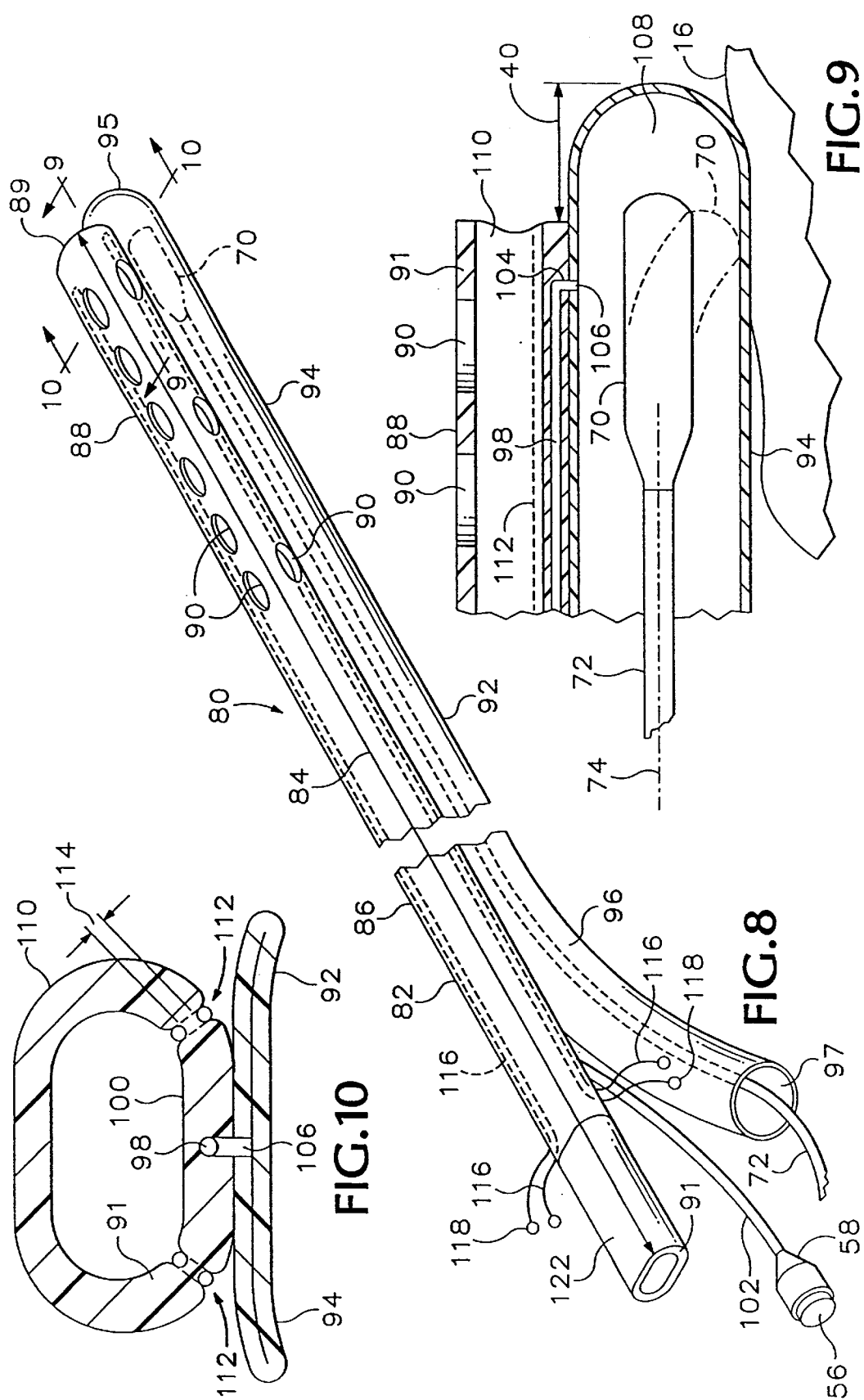

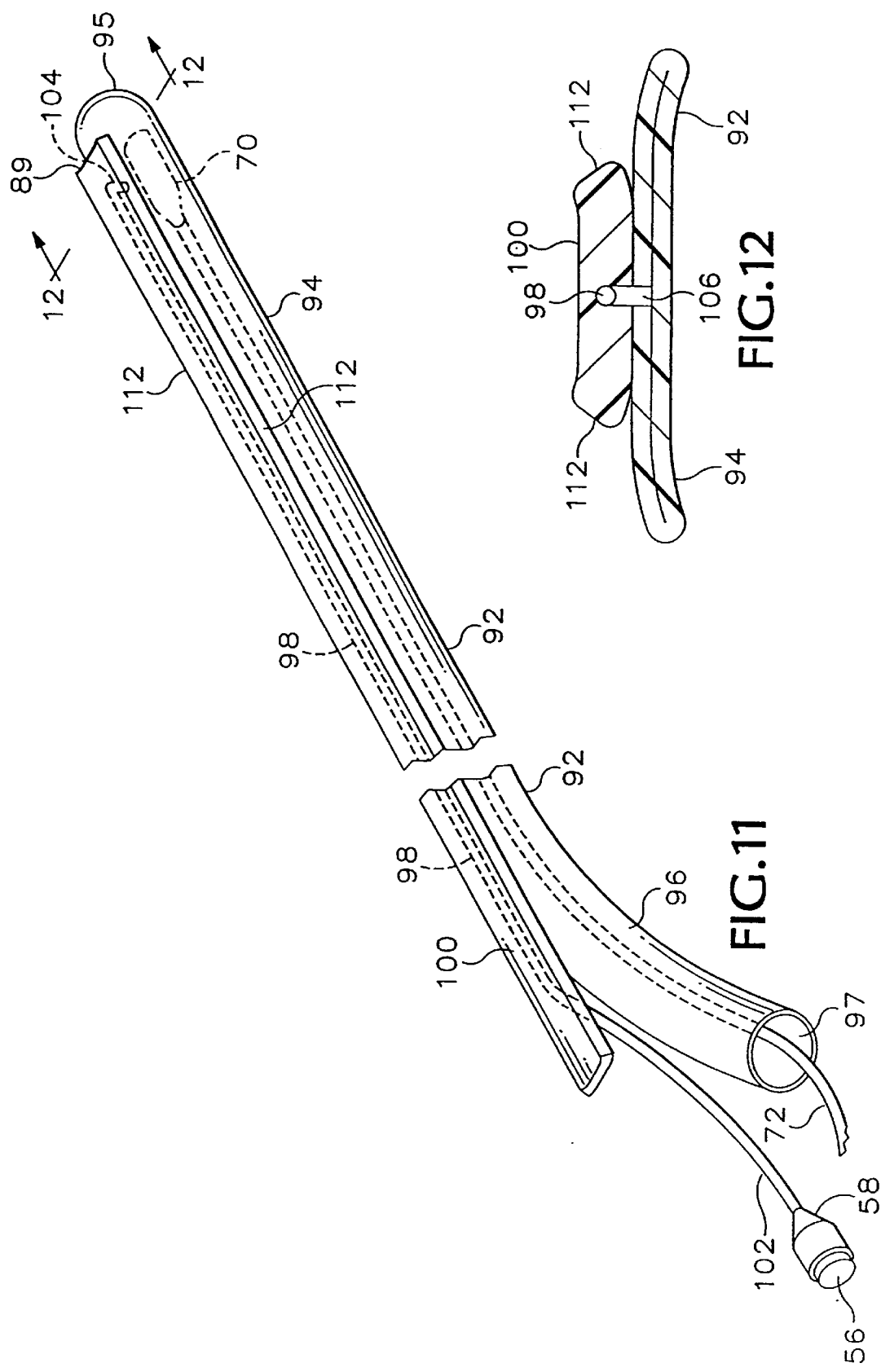

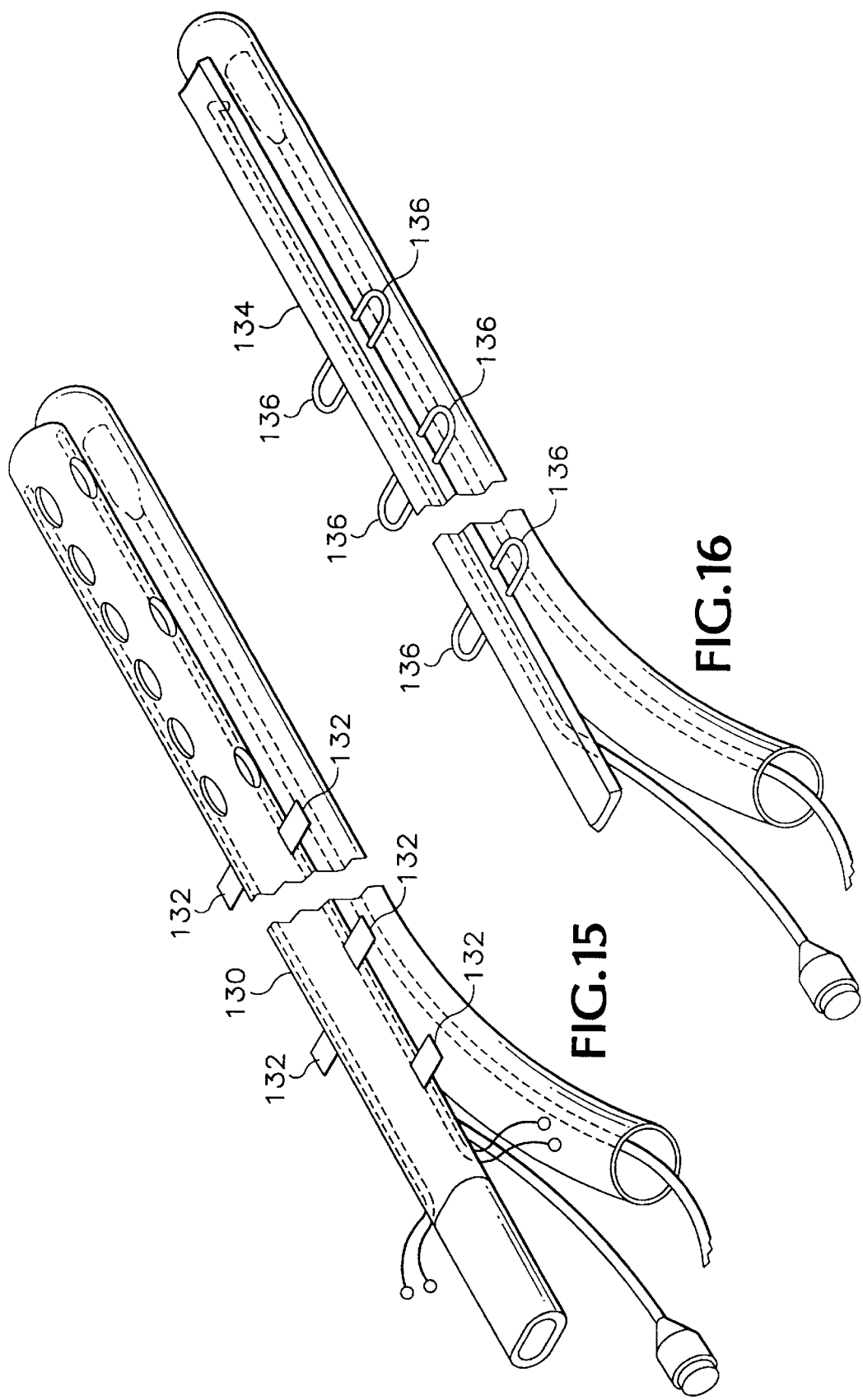

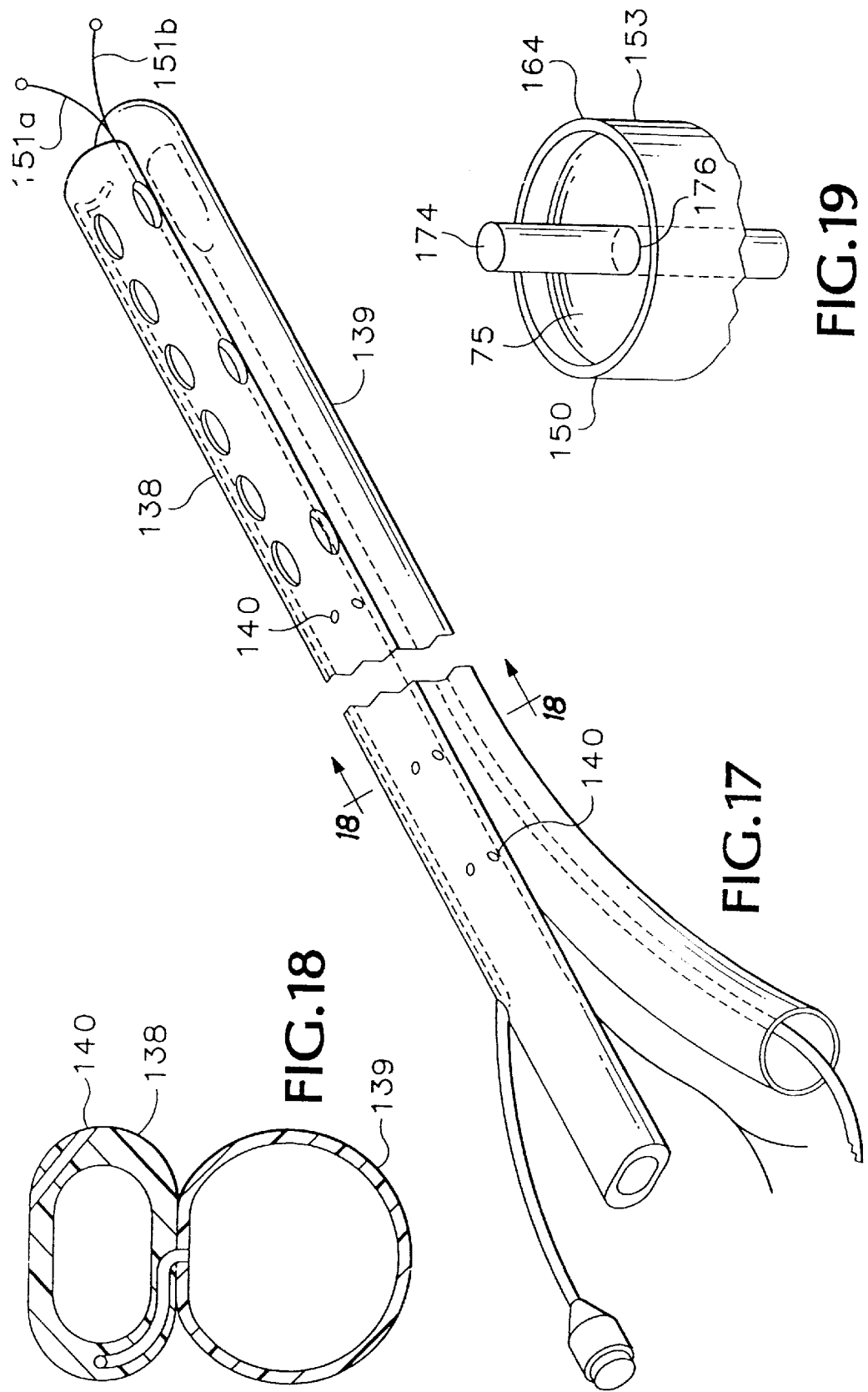

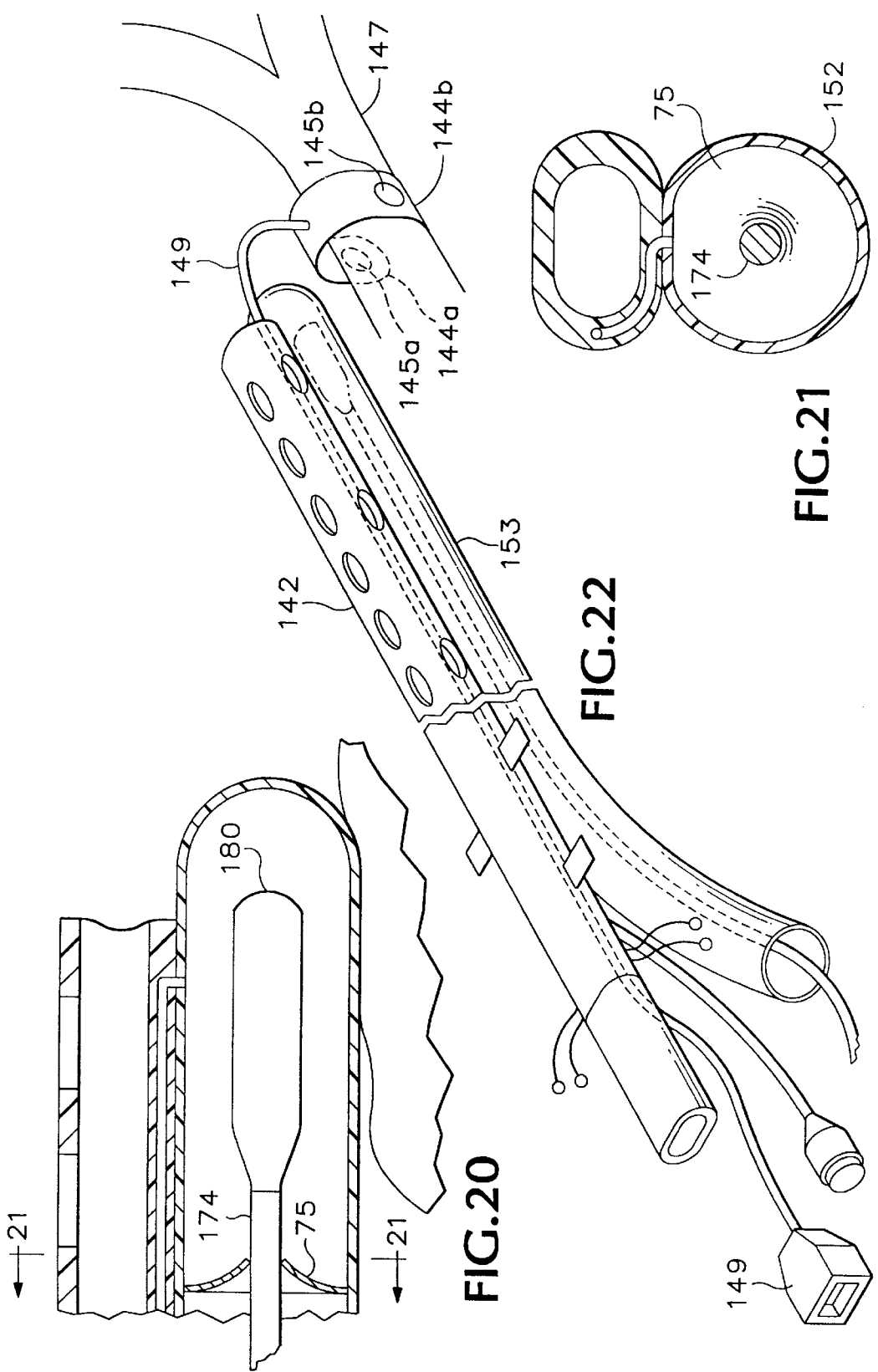

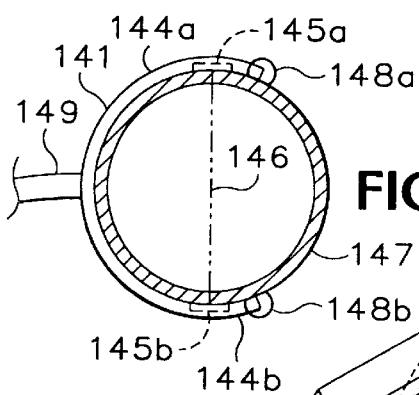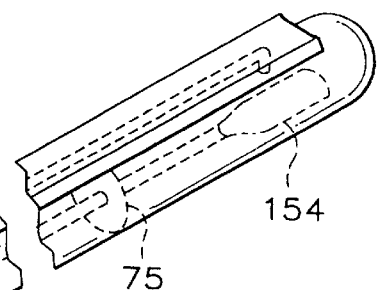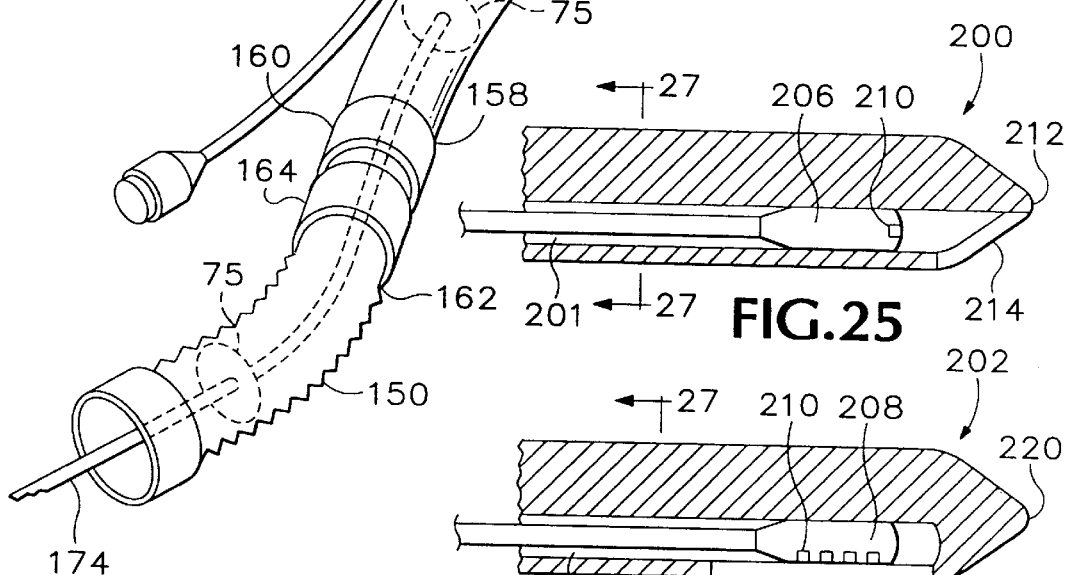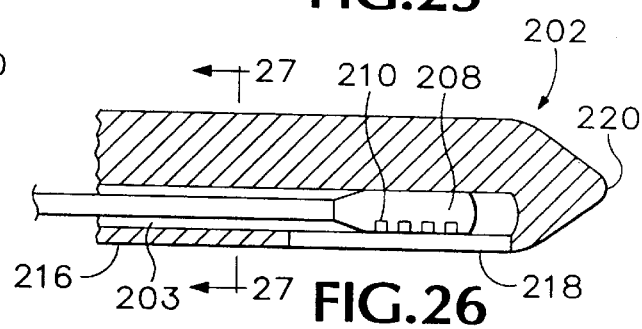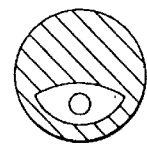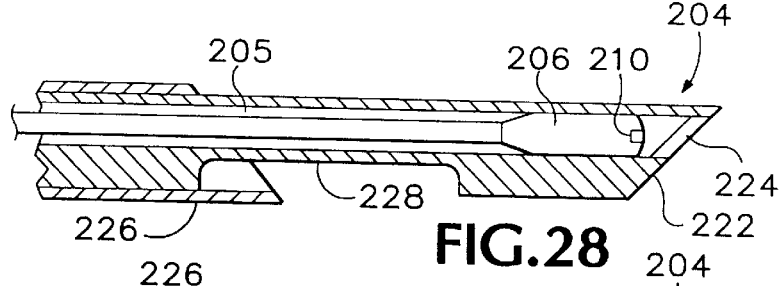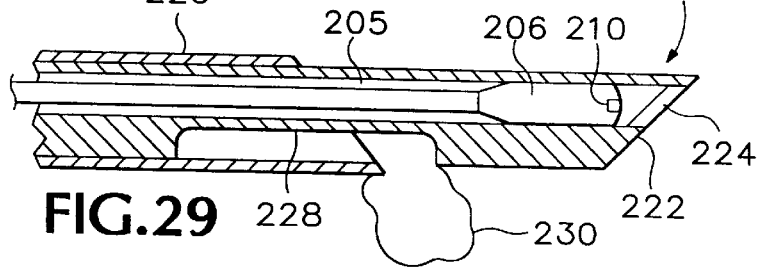

DEVICE FOR USE IN TEMPORARY INSERTION OF A SENSOR WITHIN A PATIENT'S BODY

This is a continuation-in-part of co-pending U.S. patent application Ser. No. 09/046,369, filed Mar. 23, 1998, which is a continuation-in-part of Ser. No. 08/672,484 now U.S. Pat. No. 5,775,328, filed Jun. 26, 1996 and issued Jul. 7, 1998.

BACKGROUND OF THE INVENTION

The present invention relates to placement of sensors within a patient's body, and in particular relates to facilitating repeated placement of a non-sterile sensor, such as an ultra-sound transducer, into a patient's body in a minimally invasive and sterile manner.

It is frequently desirable to obtain information regarding the size, shape, and function of internal body organs by the use of ultrasound echo imaging. For example, it is desirable to evaluate the performance of a patient's heart after cardiac surgery. In the time immediately after such surgery, patients frequently have significant cardiac functional problems, and visualization and examination of the heart by ultrasound echo imaging may be of critical value. Currently, transthoracic and transesophageal echocardiography are performed as manners of observing the heart. These are not entirely desirable, however, as the second requires sedation and presents risks of trauma to the esophagus and the images obtained by the first are of poor quality after cardiac surgery.

Fonger et al. U.S. Pat. No. 5,291,896 discloses a sterile cardiac probe inserted through an open-ended lumen of a flexible chest drain tube having one end extending into the thoracic cavity of a patient. The probe is surgically fastened to the aorta or the pulmonary artery of the patient in order to obtain information relating only to the volume of flow of blood through such vessels.

Czar et al. U.S. Pat. No. 5,205,292 discloses a removable surgically implanted sterile transducer for attachment to a blood vessel in order to evaluate the volume of blood flow in the vessel.

Abrams et al. U.S. Pat. No. 4,671,295 discloses a method and apparatus for measuring cardiac output through the use of a transducer introduced into the patient's trachea to transmit and receive ultrasound waves and evaluate the flow of blood in the ascending aorta through the use of Doppler frequency differences.

Weber U.S. Pat. No. 4,886,059 discloses an endotracheal tube including a transducer assembly disposed to transmit ultrasound waves in selected directions through the tracheal wall to collect Doppler data for blood flow velocity calculation and to calculate the diameter of the artery.

None of the devices disclosed in the patents discussed above, however, provides for placement of a non-sterile sensor such as an ultrasound transducer in a desired position within a sterile body cavity of a patient quickly, easily and repeatedly, nor does any of them provide a way of obtaining scanned ultrasound two-dimensional echo images of internal organs without having to transmit the ultra-sound waves into the body from an external location.

What is desired, then, is a device and a method for its use in permitting a non-sterile sensor such as an ultrasound scanning transducer to be introduced into a body cavity of a patient quickly and easily in a sterile fashion, and without performing additional surgical procedures or sedation as part of the introduction of the transducer. It is also desired to provide for removal and later temporary reintroduction of a non-sterile sensor without further surgical procedures or sedation.

SUMMARY OF THE INVENTION

The present invention provides an answer to the need explained above by providing a sterile probe-receiving tube which makes available a sterilely protected non-sterile space within a patient's body where a sensor probe may be inserted when necessary, either to be left in place or removed and reinserted later, as necessary. In accordance with the invention such a probe-receiving tube is supported by an elongate support member, which may have other supportive functions, attached to and extending along at least a distal portion of the probe-receiving tube, and a proximal portion of the probe-receiving tube is available outside the patient's body as an entrance through which to insert a non-sterile probe into the interior of the patient's body. In one embodiment of the invention a proximal portion of the elongate support member is available outside the patient's body for use if necessary to adjust the location of the probe enclosed within the probe-receiving tube attached to it.

In a device which is one embodiment of the invention the elongate support member is in the form of a chest drain tube placed within the thoracic cavity of a cardiac surgery patient prior to closing the patient's chest, with the proximal portion of the device being located externally of the patient's abdomen and the distal portion of the device extending through an opening in the abdominal wall and thence toward the patient's heart, so that the probe-receiving tube is available in a desired position to provide an ultrasound two-dimensional echo image of the patient's heart or continuous-wave pulse gated, and color flow Doppler ultrasound data during the post-surgery period when it is critical to evaluate the function of the heart.

In a preferred embodiment of the invention a conduit may be provided through which to introduce an acoustic coupling medium into the distal portion of the probe-receiving tube to enable a sensor utilizing sound waves, such as an ultrasound transducer probe, to be operated efficiently. Since the distal end of the probe-receiving tube of a device according to the invention is closed, the internal space within the probe-receiving tube is isolated from the interior of the patient's body cavity, and introduction of a non-sterile sensor probe or of material introduced through the conduit as an acoustic coupling agent cannot result in contamination of the patient's body cavity.

In a device that is another embodiment of the invention a support member includes a separable part and may include a cutting device by which the separable part can be removed easily from the support member and the probe-receiving tube once it is located in a desired position, leaving a support member of reduced size attached to the probe-receiving tube.

In accordance with the method of the invention a sensor probe can be placed quickly and easily in a desired location within a patient's body by inserting it into the patient's body through the probe-receiving tube at any time after the probe-receiving tube, supported by the elongate supporting member, has been installed.

Thus, according to the method of the invention, a non-sterile ultrasound probe may be inserted through the probe-receiving tube into a position proximate an internal organ such as a patient's heart to obtain an ultrasound echo image of the organ, as for providing an ultrasound image of the heart at a time subsequent to the completion of cardiac surgery.

Once the probe-receiving tube is in a required location, part of a support member is removed in accordance with the method of the invention, and the probe-receiving tube is left in place, supported by a support member of reduced size, but ready to receive a sensor probe quickly when needed.

In a separate preferred embodiment of the present invention, the elongate support member has at least one integrated fastening mechanism suitable to anchor the device within the patient's body. The fastening mechanism may be, for example, a transversely-extending fastener passageway, a suture wing, a suture loop, or a suture passageway. If a plurality of fastening mechanisms are used, they may be attached in an alternating step-wise arrangement or in pairs on opposite longitudinal sides of the exterior surface of the elongate support member.

In yet another separate preferred embodiment of the present invention a sterile sensor that may be attached directly to an interior blood vessel or a pair of sterile temporary pacing wires that may be attached directly to a heart is interconnected with an elongate support member and/or a probe-receiving tube. A method of the present invention for using the sterile sensor to measure a property of the blood within an internal blood vessel includes interconnecting a first finger projection having an emitter therein to a first side of the blood vessel and a second finger projection having a receptor therein to a second side of the blood vessel.

Separate preferred embodiments of the probe-receiving tube may include one or more of the following features: a flexible extension sleeve may be attached thereto; at least one hydrostatic valve may be positioned therein; and alternate sensors such as an ultrasonic sensor, a light emitting sensor, or a multi-function combination sensor may be used therein. Further, the distal end may be entirely signal transparent or may have a window defined therein that is signal transparent.

Yet another separate aspect of the present invention is the provision of a guidable surgical device such as a forward-looking guidable trocar, a laterally-looking guidable trocar, and a guidable biopsy needle. These devices have a probe-receiving tube extending longitudinally therein that is suitable for receiving a sensor probe, the sensor probe being used for guiding the guidable device.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a simplified view of a patient's torso, showing a device embodying the present invention in place.

FIG. 2 is a perspective view of a combined chest drain tube and probe-receiving tube according to the present invention.

FIG. 3 is a sectional view of part of a distal end portion of the combined chest drain tube and probe-receiving tube shown in FIG. 2.

FIG. 4 is a side elevational view of the combined chest drain tube and probe-receiving tube shown in FIGS. 1–3, with the probe-receiving tube shown in sectional view.

FIG. 5 is a sectional view, taken along line 5—5 of FIG. 2.

FIG. 6 is a sectional view taken along line 5—5 of FIG. 2, with the distal end portion of the probe-receiving tube in a collapsed condition.

FIG. 7 is a simplified view showing a short portion of the combined drain tube and probe-receiving tube shown in FIG. 1, with the combined tubes extending through the abdominal wall of a patient, and showing a suture holding the drain tube in its required location.

FIG. 8 is a perspective view of a combined chest drain tube and probe-receiving tube which is another embodiment of the present invention.

FIG. 9 is a sectional view of a part of a distal end portion of the combined chest drain tube and probe-receiving tube shown in FIG. 8.

FIG. 10 is a sectional view, taken along line 10—10 of FIG. 8, with the distal end portion of the probe-receiving tube in a collapsed condition.

FIG. 11 is a perspective view of the probe-receiving tube and a portion of the chest drain tube shown in FIG. 8, a separable portion having been removed from the chest drain tube in accordance with the present invention.

FIG. 12 is a sectional view taken along line 12—12 of FIG. 11, with the distal end portion of the probe-receiving tube in a collapsed condition.

FIG. 15 is a perspective view of a drain tube with suture wing fastening mechanisms.

FIG. 16 is a perspective view of a drain tube with suture loop fastening mechanisms.

FIG. 17 is a perspective view of a drain tube with suture passageway fastening mechanisms and pacing wires attached thereto.

FIG. 18 is a sectional view of the drain tube with suture passageway fastening mechanisms, taken along line 18—18 of FIG. 17.

FIG. 19 is a perspective view of an exemplary hydrostatic valve.

FIG. 20 is a sectional view of a part of a distal end portion of a probe-receiving tube with a hydrostatic valve therein.

FIG. 21 is a sectional view of the distal end portion of a probe-receiving tube looking towards an exemplary hydrostatic valve taken along line 21—21 of FIG. 20.

FIG. 22 is a perspective view of a sterile blood property sensor attachment of the present invention.

FIG. 23 is a sectional view of the sterile blood property sensor attachment.

FIG. 24 is a perspective view of a probe-receiving tube with an extension sleeve of the present invention attached thereto.

FIG. 25 is a sectional view of a forward-looking guidable trocar of the present invention.

FIG. 26 is a sectional view of a laterally-looking guidable trocar of the present invention.

FIG. 27 is a sectional view of the guidable trocars of FIGS. 25 and 26 taken along line 27—27.

FIG. 28 is a sectional view of a preferred embodiment of a guidable biopsy needle of the present invention in an open position.

FIG. 29 is a sectional view of the embodiment of the guidable biopsy needle of the FIG. 28 in a closed position.

DETAILED DESCRIPTION OF THE PREFERRED EMBODIMENT

Figure 13:
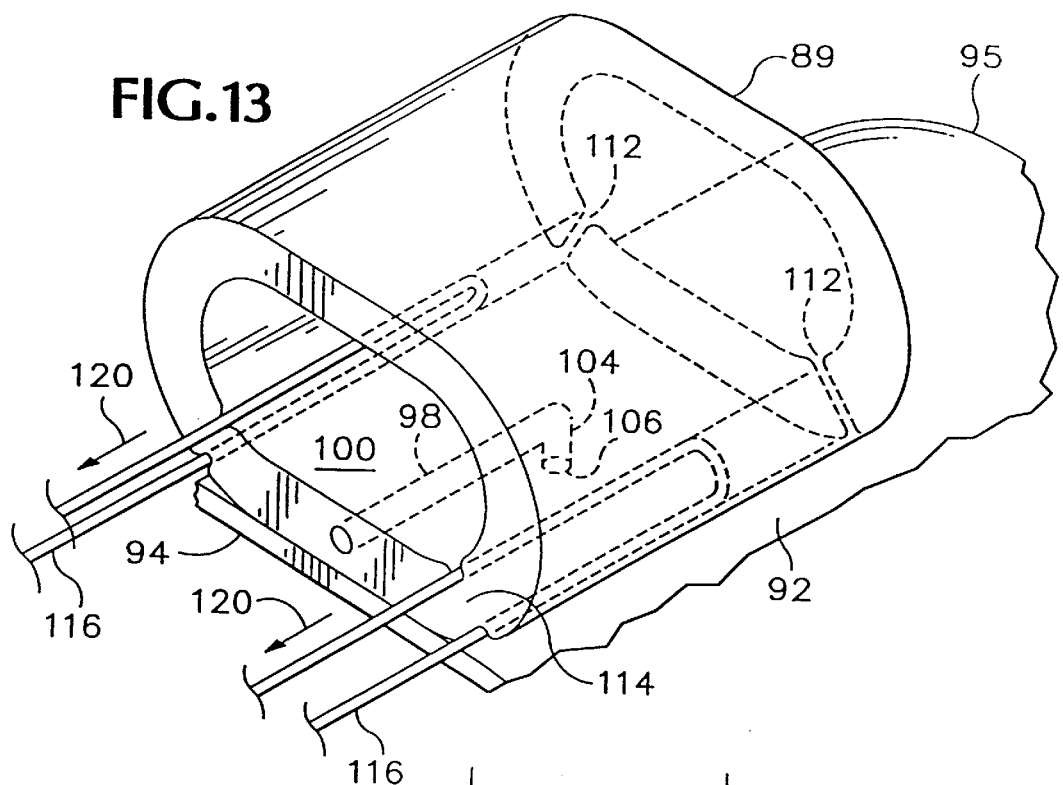
FIG. 13 is a partially cut-away view of part of the chest drain tube and probe-receiving tube shown in FIG. 8, at an enlarged scale.
Figure 14:
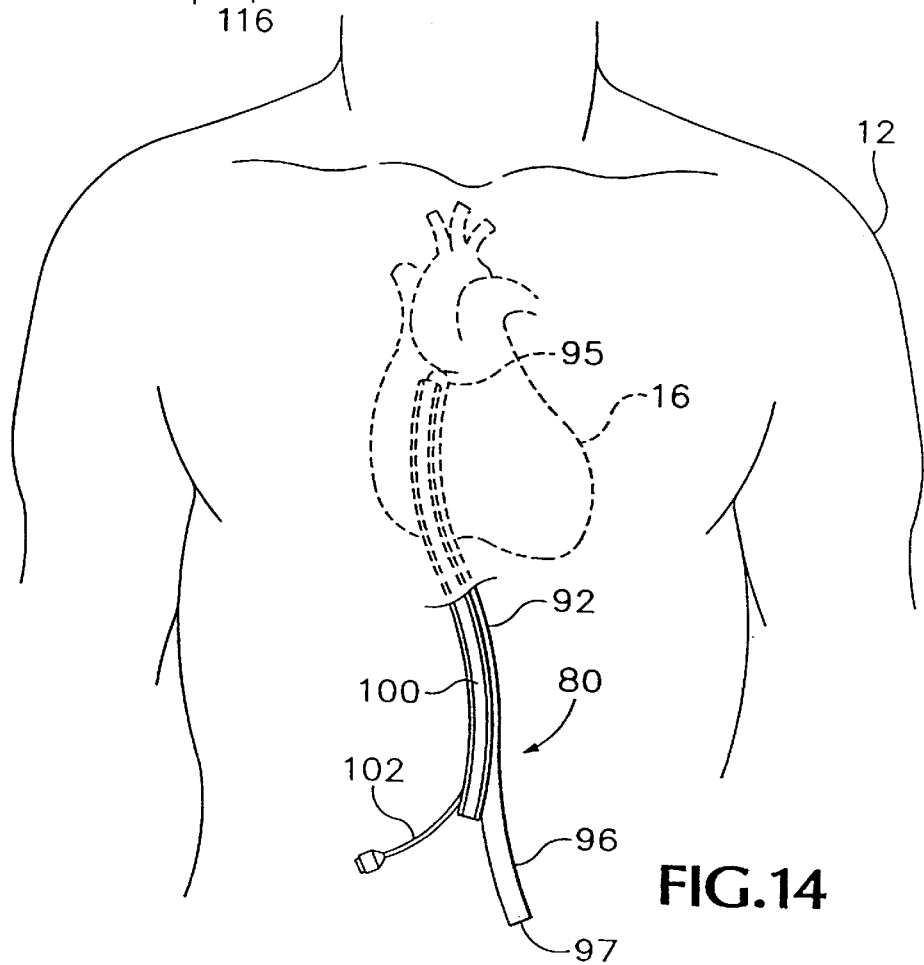
FIG. 14 is a simplified view of a patient's torso, with the device shown in FIG. 11 in place.

Referring now to the drawings which form a part of the disclosure herein, an access-providing device 10 embodying the present invention is shown in place in a cardiac surgery patient 12, with the device extending into the interior of the thoracic cavity of the patient 12 through a surgical opening 14 beneath the sternum, so that a sensor can later be positioned within the device 10 in a desired location within the thoracic cavity of the patient, in order to obtain, for example, an ultrasound image of the patient's heart 16.

As shown in greater detail in FIGS. 2, 3, and 4, the device 10 includes a chest drain tube 18, preferably of a type manufactured by Axiom Medical, Inc., of Rancho Dominguez, Calif. Such a chest drain tube 18 is of a resiliently flexible silicone rubber material which is clear and translucent and suitable for biomedical applications. One satisfactory material for the drain tube 18 has, for example, a Shore A hardness of 60±5 durometer, at least 1100 psi tensile strength, at least 600% elongation, and tear-resistance of at least 130 pounds per inch. These characteristics are not critical, but what is necessary is for the drain tube 18 to be suitable for biomedical use and to be somewhat flexible. The chest drain tube 18 shown herein as an example has a length 20 of about 445 mm and is oval in cross-section, having a width 22 of about 1.8 cm and a height 24 of about 9 mm, but these dimensions are not critical to the present invention. A maximum wall thickness 26, at one end of the oval cross-section shape, may be about 2.5 mm.

A proximal portion 28 of the chest drain tube 18 normally remains outside the body of a patient, while the drain tube 18 extends through the surgical opening 14 and a distal end portion 30 is in position in the pericardial space to remove blood following open heart surgery. The blood can enter into the lumen of the chest drain tube through the open distal end 32 and several openings 34 defined through the wall of the distal end portion 30.

Extending along and attached to the distal end portion 30 and a part of the proximal portion 28 is a probe-receiving tube 36, for which the chest drain tube 18 acts as an elongate support member. The probe-receiving tube 36 is of a biologically compatible and ultrasound translucent material such as a silicone rubber similar to that of the chest drain tube 18, in a preferred embodiment of the invention. In a separate preferred embodiment of the invention, a probe-receiving tube may be made of any material translucent with respect to a relevant frequency of light to allow the use of light emitting sensors. In yet another separate preferred embodiment of the invention, a probe-receiving tube may be made of any material permeable to both sound and light to allow the use of sound and/or light emitting sensors. Such materials should not absorb or reflect the relevant frequencies of sound or light, and may include various plastic resins or types of rubber.

The probe-receiving tube 36 has a thin, flexible wall and is generally oval or circular in cross-section, as may be seen best in FIG. 5. It has a closed distal end 38 which may be generally hemispherical, and which extends beyond the open distal end 32 of the drain tube 18 by a distance 40 of at least about 5 mm and preferably about 5 mm. A distal portion 42 and the closed distal end 38 of the probe-receiving tube 36 have a wall thickness 44 of about 0.4 mm and an inside diameter 46 of about 16 mm (36 French). The wall thickness 44 is small enough that it allows the distal portion 42 of the probe-receiving tube 36 to collapse easily or to conform easily to the shape of an object pressing against its outside surface. As may be seen most clearly in FIG. 4, a proximal portion 48 of the probe-receiving tube 36 has a length 51 of about 28 cm and has a greater wall thickness 50, for example 1.2 mm so that it has a greater tendency to retain its circular shape, for reasons which will be made apparent presently.

The distal portion 42 has a length 53 of about 24 cm, for example. The distal portion 42 and a part of the proximal portion 48 of the probe-receiving tube 36 extend along and are securely adhered to the chest drain tube 18, as shown best in FIGS. 4, 5 and 6.

A small tubular conduit 52 is defined within the wall of the chest drain tube 18 and communicates with a branch tube 54 extending away from the proximal portion 28. The branch tube 54 may be closed off tightly, as by a plug 56 fitting in an end coupling 58 which may be formed as an integral part of the branch tube 54. Near the distal end 32 of the drain tube 18, an interconnecting portion 60 of the small conduit 52 extends circumferentially of the drain tube 18 within its wall to an internal port 62, shown in FIGS. 3, 5 and 6, opening into the interior space 64 within the probe-receiving tube 36.

Preferably, the interior surface 63 of the probe-receiving tube 36, defining an interior space 64, is coated with a friction-inhibiting material which makes the interior surface very slippery when it is wetted by water or blood. This material resists adhesion and clotting of blood and is also used on the interior and exterior surfaces of the chest drain tube 18. A coating material suitable for this purpose is a polyvinylpyrollidone-polyurethane interpolymer, as disclosed in Micklus et al. U.S. Pat. No. 4,100,309, for example, available from Axiom Medical, Inc. of Rancho Dominguez, Calif. under the trademark Clot-Stop.

The proximal end part 65 of the proximal portion 28 of the chest tube 18, extending proximally from the point of insertion of the branch tube 54, does not include a lumen corresponding to small conduit 52. The proximal end part 65 may be formed as a separate piece of similar tubing without such a small lumen, joined to the portion of the chest drain tube 18 which does include the small conduit 52, so that there is no open end of the small conduit 52 exposed to possible contamination.

As shown in FIGS. 4 and 7, a transversely-extending fastener passageway 66 is defined between the chest drain tube 18 and the probe-receiving tube 36, to permit a suture 68, or a similar fastener, to encircle the chest drain tube 18 to fasten it in place where it extends through the surgical opening 14, as shown in FIG. 7, without constricting the probe-receiving tube 36.

FIGS. 15, 16, and 17 show alternative fastening mechanisms that are suitable to anchor a drain tube by suturing, sewing, stitching, stapling, or by another securing operation. First, FIG. 15 shows a drain tube 130 (which may be any of the drain tubes discussed herein, or an alternate drain tube) with a plurality of suture wings 132 thereon. The shown suture wings 132 are arranged on the drain tube in an alternating step-wise arrangement. Alternatively, the suture wings could be arranged as one or more pairs, one of each pair on opposite sides of the drain tube 130. The shown suture wings 132 are approximately 1 cm×2 cm and 5 mm thick, however, the size and thickness of the tabs would be dependent on the material of the tab and the particular use of the drain tube. FIG. 16 shows a drain tube 134 (which may be any of the drain tubes discussed herein, or an alternate drain tube) with a plurality of suture loops 136 thereon. The shown suture loops 136 are arranged as a plurality of pairs, one of each pair on opposite sides of the drain tube 134. Alternatively, the suture loops could be arranged on the drain tube in an alternating step-wise arrangement. FIG. 17 shows a drain tube 138 (which may be any of the drain tubes discussed herein, or an alternate drain tube) with a plurality of suture passageways 140 defined by a mold used to make the drain tube 138, or bored, drilled, or otherwise formed through the walls thereof. The shown suture passageways 140 are arranged on the drain tube in an alternating step-wise arrangement, but could be arranged as one or more pairs, the ones of each pair being on opposite sides of the drain tube 138. FIG. 18 is a sectional view of the drain tube 138 with a diagonally bored suture passageway 140. The suture wings. 132, suture loops 136, and suture passageways 140 are used to fasten a drain tube in place where it extends through the surgical opening 14 without constricting the probe-receiving tube.

Referring once more to FIG. 1, the access-providing device 10 may be used for a patient whose chest has been opened for cardiac surgery, by inserting the distal end part 30 of the drain tube 18, together with the attached distal portion 42 of the probe-receiving tube, through the surgical opening 14 and into the pericardial space within the patient 12. A suture 68 or other securing device is used to fasten the device 10 in place with the proximal portion 48 of the probe-receiving tube 36 preferably resting against the right ventricle of the patient's heart 16. The openings 34 are thus left available, unobstructed, to provide the required drainage of the pericardial space once the patient's chest has been closed in completion of surgery. The probe-receiving tube 36 is thus kept properly located and available to receive a probe such as a steerable ultrasound transducer probe 70, other types of ultrasonic sensors, light emitting sensor, or a multi-function combination sensor which can be inserted into the distal end 43 of the probe-receiving tube 36, supported by an encapsulated cable 72 of conventional form. The size of the interior space 64 defined within the probe-receiving tube 36 is ample to admit an ultrasound probe 70 of the size and type well known for use transesophageally in adults, such as probes including a piezoelectric transducer available from Hewlett-Packard, Advanced Technology Laboratory, or Accuson. A transducer probe 70 of smaller size may be utilized if available. The transducer cable 72 is preferably of a type which is controllably bendable and allows the transducer probe 70 to be reoriented to transmit ultrasound vibrations in various directions as illustrated by the position of the transducer probe 70 shown in broken line in FIG. 3. Additionally, the cable 72 and the ultrasound transducer probe 70 may be rotated about the longitudinal axis 74 of the cable 72, to obtain an ultra-sound image in a desired direction. The distal end portion 38 of the probe-receiving tube 36, extending beyond the distal end 32 of the drain tube 18, permits unobstructed transmission and reception of the ultrasound waves by the transducer probe 70 in any direction relative to the axis 74.

Preferably, the usual placement of the chest drain tube 18, extending into the body cavity of the patient 12 through the right rectus muscle and fascia in an orientation slightly divergent from vertical, brings the probe-receiving tube 36 into contact with the anterior surface of the epicardium of the right ventricle of the patient's heart 16. The position of the access-providing device 10 can be adjusted by the surgeon during surgery, before closure of the chest, and the suture 68 can be used to keep the entire device 10 in the proper location, to permit repeated insertion and removal of the transducer 70 through the probe-receiving tube 36 so long as the device 10 is left in place.

To assure good acoustic coupling, particularly where the transducer 70 may not be in intimate contact with the interior surface 63 of the probe-receiving tube 36, a quantity of a liquid acoustic coupling medium, such as water, may be introduced into the branch tube 54 through the end coupling 58 to displace air surrounding the transducer probe 70 within the interior space 64. As will be discussed below, the probe-receiving tube may include one or more hydrostatic valves 75 such as those shown in FIGS. 19–21, 24 to prevent leakage of the liquid coupling medium therefrom.

The greater wall thickness 50 in the proximal portion 48 of the probe-receiving tube 36 provides additional ability to resist collapsing during insertion of a probe such as an ultrasound transducer. This facilitates pushing the probe 70 and its cable 72 into the proper position within the probe-receiving tube 36, without wrinkling the part of the proximal portion 48 that is unattached to the drain tube 18. The portion of the probe-receiving tube 36 which is securely attached along side the drain tube 18 is less likely to wrinkle and impede insertion of the probe transducer 70, particularly if the interior surface of the probe-receiving tube 36 is coated with the previously-described friction-reducing coating and has been wetted as by insertion of fluid through the branch tube 54 and the small conduit 52. Since the interior space 64 within the probe-receiving tube 36 is entirely isolated from possible contact with the interior of the body of the patient 12, it need not be sterile, and it is possible to insert the ultrasound transducer probe 70 temporarily into the probe-receiving tube 36 at various times as required or desired for observation of the function of the patient's heart following surgery. Therefore, it is not absolutely necessary to keep the proximal end 49 closed and clean.

When the probe 70 and its cable 72 are not located within the interior space 64, the distal portion 48 of the probe-receiving tube 36 is free to collapse under the pressures encountered within the body cavity where the probe-receiving tube is located, as shown in FIG. 6. At the same time, the greater wall thickness 50 keeps the proximal portion of the probe-receiving tube 36 open to receive a transducer probe 70 and cable 72.

When the drain tube and the probe-receiving tube are no longer needed the suture 68 may be removed releasing the device 10 to be withdrawn, and the opening 14 can be closed.

While the invention has been described above in connection with one preferred embodiment, it will be understood that the probe-receiving tube 36 of the invention may be unsupported or supported by an elongate support member of a different construction and can be utilized for repeated temporary insertion and removal of a medical sensor such as an ultrasound transducer probe in different internal cavities of the body of a patient 12 either briefly or over an extended time of as much as several days. The probe-receiving tube of the invention thus can be used in order to scan organs within the patient's body with ultrasound or provide ultrasound transmissions for purposes of obtaining Doppler measurements, either through an opening such as the surgical opening 14, or through a natural orifice of the patient's body, such as the trachea, urethra and bladder, or rectum, so that ultrasound wave propagation to and from the organ is more direct than when transmitted through the patient's skin and layers of external tissue or bones.

For example, one such variation is illustrated in the form of an access-providing device 80 shown in FIGS. 8–14. First referring particularly to FIGS. 8, 9, and 10, the device 80 includes a chest drain tube 82 of, for example, a resiliently flexible silicone rubber material which is preferably clear and transparent and suitable for biomedical applications. The chest drain tube 82 has a length 84 and may be oval in cross-section shape, as shown in FIG. 10. The chest drain tube has a proximal portion 86 and a distal end portion 88 with an open end 89 and defines several openings 90 extending through the wall 91 of the distal end portion 88 and communicating with the lumen of the drain tube 82 to allow material to enter the drain tube to be drained from a patient's body cavity.

Extending closely alongside and attached to the chest drain tube 82, along its distal end portion 88 and a part of its proximal end portion 86, is a probe-receiving tube 92 essentially similar to the probe-receiving tube 36 of the access-providing device 10 described above. A distal portion 94 and a part of a proximal portion 96 of the probe-receiving tube 92 are securely adhered to the chest drain tube 82 as by being thermally fused during manufacture of the device 80, with a closed distal end 95 extending a short distance beyond the distal end 89 of the drain tube 82. A proximal end 97 of the probe-receiving tube 92 is open, to receive a sensor probe such as an ultrasound transducer 70 and its cable 72.

A small tubular conduit 98 is similar to the conduit 52 described in connection with the access-providing device 10, but is located in a base portion 100 of the chest drain tube 82. The base portion 100 is the part of the chest drain tube 82 extending along and located most closely adjacent to the probe-receiving tube 92, to which the base portion 100 is directly attached. A branch tube 102, similar to the branch tube 54, extends from the base portion 100 of the chest drain tube 82, near the proximal end 86, and communicates with the small conduit 92. Near the distal end portion 88 of the chest drain tube 82 an interconnecting portion 104 of the small conduit 98 extends through an internal port 106 into the interior space 108 within the probe-receiving tube 92 so that the branch tube 102 and the conduit 98 can be used to supply an acoustic coupling fluid or contrast medium to the space 108. The probe-receiving tube may include one or more hydrostatic valves 75 such as those shown in FIGS. 19–21, 24 to prevent leakage of the liquid therefrom.

A separable portion 110 of the chest drain tube 82 is removable from the base portion 100. The separable portion extends longitudinally of the chest drain tube 82 and is delineated by a separation region 112 including an interface between the separable portion 110 and the base portion 100. The material of the drain tube 82 in the separation region 112 is intended to fail more easily than the adjacent portions of the drain tube 82 to allow the separable portion 110 to be removed easily from the base portion 100. The separation region 112 may be defined by appropriately shaping the chest drain tube 82 so that a linear region has a lesser wall thickness, as at 114, and thus has a lesser strength than adjacent portions of the wall 92 of the chest drain tube 82, so that the separable portion 110 can be torn apart from the base portion 100 under a definite force that is small enough not to disturb the location of the distal portion 94 of the probe-receiving tube 92. It may be desirable to initiate such tearing by making a small cut in the drain tube wall in the separation region 112 when it is desired to remove the separable portion 110 from the base portion.

Preferably, however, a long U-shaped cutting element in the form of a flexible, thin, yet strong filament 116 is embedded in the wall of the drain tube 82 along each side of the base part 100 with the base of the "U" shape located in the distal end portion 88. The filament 116 may be of a synthetic fiber material of suitable tensile strength, or may be a suitably fine, flexible metal wire. At least one end of each filament 116 should be kept available near the proximal end portion 86 of the drain tube 82. The end of the filament 116 may include an attached bead-like end piece 118 to facilitate grasping at least the inner end of the filament 116 so that it can then be pulled, as indicated by the arrows 120, toward the proximal end portion 86 of the drain tube 82, causing the "U"-shaped portion to move progressively along the separation region 112 to cut free the separable part 110 of the drain tube 82, as shown in FIG. 13. The portion 122 of the proximal end portion of the drain tube 82 may easily be cut off as by scissors for convenience, to leave the base 100 as shown in FIG. 11. The base 100 thus remains as a smaller support member, more slender than the drain tube 82, and also shorter if the proximal portion 122 is removed.

In situations where it may be desired to observe the initial placement of the probe-receiving tube 92 and the attached support member radiographically, the filaments or cutting elements 116 should be of metal wire or another radiopaque material, so as to make the location of the distal end of the probe-receiving tube 92 readily apparent.

While use of a chest drain tube 82 may be necessary for a time following a surgical procedure such as a heart-valve replacement, once the drainage function is no longer required the separable portion 110 of the drain tube 82 may be removed from the base portion 100 and withdrawn from the chest cavity of the patient, leaving the base part 100 in place as a support member of reduced size attached to the probe-receiving tube 92 during a further time when it may be desired to use a sensor probe such as an ultrasound transducer. The reduced size of the support member then will promote patient comfort while preserving the possibility of quickly placing a sensor probe into the required location.

It will be understood that in other situations it may also be desirable to leave a probe-receiving tube 92 in a location where a support element of small size is sufficient once the probe-receiving tube 92 is in the required location, while a larger support member that need not be a drain tube is desired to be used during initial placement of a probe-receiving tube. A portion of such a support member may thus be removable by the use of a single cutting element 116 to leave behind a base portion 100 together with the probe-receiving tube 92 once it has been positioned appropriately.

FIGS. 22 and 23 are directed to a sterile blood property sensor 141 that can be attached to a drain tube or a probe-receiving tube such as those described above and indicated generally as drain tube 142 and probe-receiving tube 143. The sensor 141 is preferably a flexible device with at least two fingers 144a and 144b. One finger 144a would include an emitter 145a such as a light emitting diode and the other finger 144b would include a receptor 145b suitable for receiving the emitted signal 146 from the emitter 145a. Like external oxygen saturation sensors that are used to measure oxygen saturation by being wrapped around a finger, the sensor is wrapped directly around blood vessel 147 such as a vein or artery such as the pulmonary artery or the Vena Cava so as to measure a property of the blood, such as oxygen saturation, in the blood vessel. The sensor 141 can also be one used to measure other blood conditions pertaining, for example, to hemoglobin, glucose, and potassium. During surgery, after the drain tube 142 has been placed in the patient's body, the fingers 144a and 144b are sutured, stapled or otherwise secured on opposite sides of a blood vessel 147 using fine sutures 148a, 148b or other securing mechanisms. The emitter 145a then emits a signal that is received by the receptor 145b. The signal may then be transmitted to a computer or specialized medical device through a connector cable 149. It should be noted that the sensor 141 is particularly suited to be used in conjunction with the separable embodiment of the probe-receiving tube according to the invention as shown and described in connection with FIGS. 8–16.

Other sterile medical devices may be attached to a drain tube, probe-receiving tube, or other elongate support member. For example, temporary pacing wires 151a, 151b (FIG. 17) may run longitudinally between a drain tube 138 and an attached probe-receiving tube 139. During surgery, after the drain tube 138 has been placed in the patient's body, the ground pace wire 151a and the signal pace wire 151b are sutured, stapled or otherwise secured on opposite sides of a patient's heart (not shown) using fine sutures (not shown) or other securing mechanisms.

Where a sensor 141 or pacing wires 151a, 151b are utilized during a surgical procedure where a probe receiving tube or a drain tube that is to be left in place following the procedure, such an associated sensor 141 or pacing wires are attached to the patient's tissue delicately so that the sensor 141 or pacer wires 151a and 151b can be removed along with the drain tube or probe receiving tube as by merely slipping the pacer wires from sutures, or breaking fine sutures to remove the sensor 141. Thus the sensor or pacer wires can be removed from a patient without reopening the body cavity.

In situations where the aforementioned probe-receiving tubes are to be used during surgery, or in other situations where external sterility is important, a flexible extension sleeve 150 may be used so that a greater portion of the sensor cable 174 is enclosed in a sterile sleeve. FIG. 24 shows an exemplary probe-receiving tube 152 (which may be any of the probe-receiving tubes discussed herein or an alternate probe-receiving tube) with an attached extension sleeve 150. A sensor 154 (which may be any sensor discussed herein or an alternate sensor), which may or may not be sterile, may be inserted through the extension sleeve 150 into the probe-receiving tube 152. Preferably the external surface 156 of the sleeve 150 is sterile so that the sleeve 150, with the sensor 154 therein, may be manipulated without contaminating the user. The extension sleeve 150 may be removable or non-removable. For a removable embodiment, the proximal tube end 158 of the tube 152 includes a tube connecting apparatus 160 and at least one sleeve end 162 of the extension sleeve 150 includes a sleeve connecting apparatus 164 suitable for mating with the tube connecting apparatus 160. The connecting apparatus 160, 164 may be any sterile, leakproof connecting apparatus. The flexible extension sleeve 150 may be similar in configuration to the collapsible sterile sleeve used in connection with percutaneous catheter introducers such as the one produced by C.R. Bard Ireland Limited of Galway Ireland.

A hydrostatic valve 75 may be positioned within said extension sleeve 150 as shown in FIG. 24 or, as set forth above, within a probe-receiving tube 152 which may be any of the probe-receiving tubes discussed herein or an alternative probe-receiving tube. The hydrostatic valve 75 provides a substantially leakproof seal so that fluids within the probe-receiving tube and/or the extension sleeve 150 cannot leak therethrough when the hydrostatic valve 75 is closed, during insertion of a sensor 154, while the sensor 154 is in proper position, during removal of the sensor 154, or after the sensor 154 has been removed. Preferably the hydrostatic valve 75 is made of shape-retaining material that can be permeated by a sensor 154, can grip the exterior surface 170 of the sensor and the exterior surface 172 of the sensor's cable 174, and then can substantially return to its original state when the sensor is removed. As shown in FIGS. 19 and 21, the hydrostatic valve 75 has a perforation 176 through which the sensor 154 is inserted.

The probe-receiving tubes discussed herein may be suitable for or adapted to accommodate alternative sensing devices 180 (FIG. 20) including, but not limited to, an ultrasonic sensor, a light emitting sensor, or a multi-function combination sensor. The sensor 180 may be one useful for sensing one or more of the following exemplary monitorable blood conditions: oxygen saturation (venous, arterial, or mixed venous and internal arterial), hemoglobin, glucose, potassium, and pH. The sensor may be a forward-looking sensor (also shown in FIGS. 25, 28, and 29) or a laterally-looking sensor (also shown in FIG. 26). The probe-receiving tube may be made entirely of any implantable, flexible material permeable to light, sound, or both light and sound, depending on the intended purpose of the sensor 180 the tube is designed to receive. Alternatively, a probe-receiving tube may include a window (such as those shown in relation to the trocars of FIGS. 25 and 26) or end portion made of such a material transparent to or permeable to light, sound, both light and sound, or other type of signal depending on the purpose of the sensor 180.

Although the probe-receiving tubes discussed above are shown as attached to a drain tube that functions as the elongate support member, an alternate elongate support member such as a trocar 200, 202 or a biopsy needle 204 may be used to support the probe-receiving tube 201, 203, or 205. Further, the probe-receiving tube 201, 203, or 205 may be integrated within the elongate support member as shown in FIGS. 25–29. Like the sensors for the drain tube elongate support members, the sensors 206, 208 for the alternate elongate support members may serve to sense or monitor oxygen saturation, hemoglobin, glucose, potassium, and pH as do the sensors described above. Further, the sensors 206, 208 serve to provide an image to the user by which the user can guide the elongate support member through body tissue. It should be noted that any of the probe-receiving tubes discussed above could be similarly guided.

The forward-looking guidable trocar 200 shown in FIG. 25, functions as an elongate support member for a probe-receiving tube 201 through which a sensor may be inserted. The shown sensor is a forward-looking sensor 206 that includes sensing apparatus 210 that face forward towards the closed distal end 212 of the forward-looking guidable trocar 200. The sensing apparatus 210 may be an ultrasonic sensor, a light emitting sensor, or a multi-function combination sensor. The distal end 212 may include a window 214 that is light permeable, sound permeable, both light and sound permeable, or other type of signal permeable or transparent depending on the type of sensor 206 to be inserted into the forward-looking guidable trocar 200. Alternatively, the entire distal end 212 or the entire forward-looking guidable trocar 200 could be made light permeable, sound permeable, both light and sound permeable, or other type of signal permeable or transparent depending on the type of sensor 206 to be inserted into the forward-looking guidable trocar 200. Preferably the forward-looking guidable trocar 200 is either sterilized or a sterile, single use trocar. The sensor 206, which does not have to be sterile since it is enclosed completely within the probe-receiving tube 201, is inserted into the probe-receiving tube 201 prior to or just after the insertion of the trocar 200 into a patient's body. Using the sensor 206, the trocar 200 is guided into a desired position. The sensor 206 may then be removed from the trocar 200 or left inside to allow for continued monitoring. When the sensor 206 is removed, it may be reused as it would not have come into contact with the patient.

The laterally-looking guidable trocar 202 shown in FIG. 26 functions as an elongate support member for a probe-receiving tube 203 through which a sensor may be inserted.

The term "laterally-looking" is meant to describe a direction radial to the longitudinal axis of the trocar 202. The shown sensor is a laterally-looking sensor 208 that includes sensing apparatus 210 that faces towards the wall 216 of the laterally-looking guidable trocar 202. The sensing apparatus 210 may be an ultrasonic sensor, a light emitting sensor, or a multi-function combination sensor. The wall 216 may include a window 218 that is light permeable, sound permeable, both light and sound permeable, or permeable or transparent to another type of signal depending on the type of sensor 208 to be inserted into the laterally-looking guidable trocar 202. Alternatively, the entire distal end 220 or the entire laterally-looking guidable trocar 202 could be made light permeable, sound permeable, both light and sound permeable, or other type of signal permeable or transparent depending on the type of sensor 206 to be inserted into the laterally-looking guidable trocar 202. The laterally-looking guidable trocar 202 would be used similarly to the forward-looking guidable trocar 200, except that it would be guided by lateral "views."

The guidable biopsy needle 204 shown in FIGS. 28–29 functions as an elongate support member for a probe-receiving tube 205 through which a sensor may be inserted. The shown sensor is a forward-looking facing sensor 206 that includes sensing apparatus 210 that face forward towards the distal end 222 of the guidable biopsy needle 204. The sensing apparatus 210 may be an ultrasonic sensor, a light emitting sensor, or a multi-function combination sensor. The distal end 222 may include a window 224 that is light permeable, sound permeable, both light and sound permeable, or other type of signal permeable or transparent depending on the type of sensor 206 to be inserted into the guidable biopsy needle 204. Alternatively, the entire distal end 222 or the entire guidable biopsy needle 204 could be made light permeable, sound permeable, both light and sound permeable, or other type of signal permeable or transparent depending on the type of sensor 206 to be inserted into the guidable biopsy needle 204. Preferably the guidable biopsy needle 204 is either sterilized or a sterile, single use biopsy needle having a biopsy sampling mechanism such as, for example, the sampling mechanism of the Tru-Cut Biopsy Needle made by Baxter Healthcare Corporation of Valencia, Calif. The sensor 206, which does not have to be sterile since it is enclosed completely within the probe-receiving tube 205, is inserted into the probe-receiving tube 205 prior to or just after the insertion of the biopsy needle 204 into a patient's body. The needle 204 is inserted into the patient's body in a closed position (not shown) with the obturator 226 fully covering the specimen notch 228. Using the sensor 206, tissue 230 to be biopsied is found and the distal end 222 is inserted through the tissue 230 so that the specimen notch 228 is within the desired tissue 230. The needle 204 is then opened as shown in FIG. 28 to expose the specimen notch 228. When the tissue 230 prolapses into the specimen notch 228, the needle 204 is closed, thereby cutting and enclosing a tissue sample within the specimen notch 228. When the sensor 206 is removed, it may be reused as it would not have come into contact with the patient.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for use in a medical procedure for placing a sensor probe temporarily in a desired location within a patient's body, comprising:
    (a) an elongate support member having a distal end portion and a proximal portion, said elongate support member having a wall with an interior surface and an exterior surface;
    (b) a probe-receiving tube longitudinally adjacent said elongate support member, said tube having a closed distal end defining an interior space within said tube and a proximal portion; and
    (c) at least one fastening mechanism integrated with said device suitable to anchor said device within the patient's body.

2. The device of claim 1 wherein said at least one fastening mechanism is at least one transversely-extending fastener passageway located between said proximal portion of said support member and said proximal portion of said probe-receiving tube.

3. The device of claim 1 wherein said at least one fastening mechanism is at least one suture wing on the exterior surface of the wall of the proximal portion of said elongate support member.

4. The device of claim 1 wherein said at least one fastening mechanism is at least one suture loop on the exterior surface of the wall of the proximal portion of said elongate support member.

5. The device of claim 1 wherein said at least one fastening mechanism is a plurality of fastening mechanisms attached to longitudinal sides of said exterior surface of said elongate support member in an alternating step-wise arrangement.

6. The device of claim 1 wherein said at least one fastening mechanism is a plurality of fastening mechanisms attached in pairs on opposite longitudinal sides of said exterior surface of said elongate support member.

7. A device for use in a medical procedure for placing a sensor probe temporarily in a desired location within a patient's body, comprising:
    (a) an elongate support member having a distal end portion and a proximal portion;
    (b) a probe-receiving tube located closely adjacent and alongside and attached to said elongate support member, said tube having a closed distal end defining an interior space within said tube; and
    (c) a sterile sensor located outside said probe-receiving tube and interconnected with said probe-receiving tube, said sensor being directly interconnect able with an interior blood vessel.

8. A device for use in a medical procedure for placing a sensor probe temporarily in a desired location within a patient's body, comprising:
    (a) an elongate support member having a distal end portion and a proximal portion;
    (b) a probe-receiving tube adjacent and alongside said elongate support member, said tube having a closed distal end defining an interior space within said tube; and
    (c) a sterile sensor located outside said probe-receiving tube and interconnected with said probe-receiving tube, said sensor being directly interconnect able with an interior blood vessel, said sensor comprising first and second finger projections, said first finger projection having an associated emitter and said second finger projection having an associated receptor, said first finger projection being attachable to a first side of said blood vessel and said second finger projection being attachable to a second side of said blood vessel, and said emitter being suitable to emit a signal through said blood vessel that said receptor is suitable to receive.

9. A device for use in a medical procedure for placing a sensor probe temporarily in a desired location within a patient's body, comprising:
   (a) an elongate support member having a distal end portion and a proximal portion;
   (b) a probe-receiving tube adjacent and alongside said elongate support member, said tube having a closed distal end defining an interior space within said tube; and
   (c) a sterile sensor located outside the probe-receiving tube and interconnected with said probe-receiving tube, said sensor being a pulmonary arterial saturation sensor for measuring oxygen saturation within an internal blood vessel and being directly interconnect able with such an interior blood vessel.

10. A device for use in a surgical procedure within a patient's body, comprising:
    (a) an elongate support member having a distal end portion and a proximal portion;
    (b) a sterile sensor interconnected with said distal portion of said elongate support member, said sensor comprising:
        (i) first and second finger projections, said first finger projection having an associated emitter and said second finger projection having an associated receptor;
        (ii) said first finger being attachable to a first side of a blood vessel and said second finger being attachable to a second side of said blood vessel; and
        (iii) said emitter being suitable to emit a signal through said blood vessel that said receptor is suitable to receive.

11. A method for measuring within an internal blood vessel, comprising:
    (a) providing a relatively stiff elongate support member having a distal end portion with an attached sterile sensor having a first finger with an emitter and a second finger with a receptor;
    (b) thereafter inserting said distal end portion of said support member together with said sterile sensor into an interior cavity or a passageway communicating with a body cavity of a living patient;
    (c) thereafter, attaching said first finger to a first side of an internal blood vessel and said second finger to a second side of said internal blood vessel; and
    (d) thereafter, said emitter emitting a signal through said internal blood vessel and said receptor receiving said signal.

12. A device for use in a medical procedure for placing a non-sterile sensor probe temporarily in a desired location within a patient's body, comprising:
    (a) an elongate support member;
    (b) a probe-receiving tube located closely adjacent and alongside and attached to said elongate support member, said tube having a sterile closed distal end defining an interior space within said tube and a proximal portion; and
    (c) a flexible extension sleeve removably attached to and communicating with said interior space within said proximal portion of said probe-receiving tube;
    (d) wherein said support member, said probe-receiving tube, and said flexible extension sleeve have sterile exterior surfaces.

13. The device of claim 12 wherein at least one hydrostatic valve is positioned within said probe-receiving tube.

14. The device of claim 12 wherein at least one hydrostatic valve is positioned within said flexible extension sleeve.

15. A device for use in a medical procedure for placing a non-sterile sensor probe temporarily in a desired location within a patient's body, comprising:
    (a) an elongate support member having a sterile distal end portion and a proximal portion; and
    (b) a probe-receiving tube located closely adjacent and alongside and attached to said elongate support member, said tube having a sterile closed distal end defining an interior space within said tube suitable for receiving said non-sterile sensor probe, at least part of said distal end being signal transparent.

16. A device for use in a medical procedure for placing a non-sterile sensor probe temporarily in a desired location within a patient's body, comprising:
    (a) an elongate support member having a sterile distal end portion and a proximal portion; and
    (b) a probe-receiving tube located closely adjacent and alongside and attached to said elongate support member, said tube having a sterile closed distal end defining an interior space within said tube suitable for receiving said non-sterile sensor probe, at least part of said distal end being signal transparent, and at least one hydrostatic valve being positioned within said probe-receiving tube.

17. A device for use in a medical procedure for placing a non-sterile sensor probe temporarily in a desired location within a patient's body, comprising:
    (a) an elongate support member having a sterile distal end portion and a proximal portion; and
    (b) a probe-receiving tube located closely adjacent and alongside and attached to said elongate support member, said tube having a sterile closed distal end defining an interior space within said tube suitable for receiving said non-sterile sensor probe, wherein said sensor probe is an ultrasonic sensor, at least part of said distal end being signal transparent to an ultrasonic signal.

18. A device for use in a medical procedure for placing a non-sterile sensor probe temporarily in a desired location within a patient's body, comprising:
    (a) an elongate support member having a sterile distal end portion and a proximal portion; and
    (b) a probe-receiving tube located closely adjacent and alongside and attached to said elongate support member, said tube having a sterile closed distal end defining an interior space within said tube suitable for receiving said non-sterile sensor probe, wherein said sensor probe includes a light emitting sensor, at least part of said distal end being signal transparent to a light signal.

19. A device for use in a medical procedure for placing a non-sterile sensor probe temporarily in a desired location within a patient's body, comprising:
    (a) an elongate support member having a sterile distal end portion and a proximal portion; and
    (b) a probe-receiving tube located closely adjacent and alongside and attached to said elongate support member, said tube having a sterile closed distal end defining an interior space within said tube suitable for receiving said non-sterile sensor probe, wherein said sensor probe is a multi-function combination sensor, at least part of said distal end being signal transparent to a plurality of signal types.

20. A device for use in a medical procedure for placing a non-sterile sensor probe temporarily in a desired location within a patient's body, comprising:

(a) an elongate support member having a sterile distal end portion and a proximal portion; and (b) a probe-receiving tube located closely adjacent and alongside and attached to said elongate support member, said tube having a sterile closed distal end defining an interior space within said tube suitable for receiving said non-sterile sensor probe, wherein at least part of said distal end is a signal transparent window defined in said closed distal end.

21. A device for use in a medical procedure for placing a non-sterile sensor probe temporarily in a desired location within a patient's body, comprising:

(a) an elongate support member having a sterile distal end portion and a proximal portion; and (b) a probe-receiving tube located closely adjacent and alongside and attached to said elongate support member, said tube having a sterile closed distal end defining an interior space within said tube suitable for receiving said non-sterile sensor probe, wherein at least part of said distal end is a signal transparent window defined in at least a portion of a wall of said probe-receiving tube located substantially adjacent said closed distal end.

22. A guidable surgical device for use in a medical procedure, comprising:

(a) an elongate support member having a support member wall and a distal end portion; and (b) a probe-receiving tube defined by said support member wall, said tube having a closed distal end defining an interior space within said tube suitable for receiving a sensor probe, at least part of said closed distal end being sensor permeable.

23. The guidable device of claim 22 wherein said probe-receiving tube is suitable for receiving a non-sterile sensor probe.

24. A guidable surgical device for use in a medical procedure, comprising:

(a) a forward-looking guidable trocar having a distal end portion; and (b) a probe-receiving tube defined by and extending within said trocar, said tube having a closed distal end defining an interior space within said tube suitable for receiving a sensor probe, at least part of said closed distal end being sensor permeable; and (c) a sensor probe located within said probe-receiving tube and having sensing apparatus directed toward said sensor permeable closed distal end of said probe-receiving tube.

25. A guidable surgical device for use in a medical procedure, comprising:

(a) an elongate laterally-looking guidable trocar having a distal end portion; and (b) a probe-receiving tube defined by and extending within said trocar, said tube having a wall and a closed distal end defining an interior space within said tube suitable for receiving a sensor probe, at least part of said closed distal end and at least part of said wall substantially adjacent said closed distal end being sensor permeable; and (c) a sensor probe located within said probe-receiving tube and having sensing apparatus directed toward said at least part of said tube wall substantially adjacent said closed distal end of said probe-receiving tube.

26. A guidable surgical device for use in a medical procedure, comprising:

(a) a guidable biopsy needle having a distal end portion; and (b) a probe-receiving tube defined by and extending within said biopsy needle, said tube having a wall and a closed distal end defining an interior space within said tube suitable for receiving a sensor probe, at least part of said closed distal end being sensor permeable; and (c) a sensor probe located within said probe-receiving tube and having sensing apparatus directed toward said sensor permeable part of said closed distal end of said probe-receiving tube.

27. A method for guiding a guidable surgical device in a medical procedure, comprising:

(a) providing a guidable surgical device with a probe-receiving tube defined within an elongate support member with a distal portion, said tube having a sensor permeable closed distal end defining an interior space within said tube suitable for receiving a sensor probe;

(b) inserting said distal portion of said support member together with said sensor permeable closed distal end of said tube into an interior cavity or a passageway into a body cavity of a patient;

(c) temporarily inserting a sensor probe within said probe-receiving tube and into proximity with said sensor permeable closed distal end thereof; and (d) using said sensor probe to guide said guidable surgical device to a desired location within said patient while said sensor probe is within said probe-receiving tube.

28. The method of claim 27 further comprising the step of utilizing said sensor probe to make a desired observation within said patient.

29. The method of claim 27 wherein said step of inserting said distal portion of said support member together with said closed distal end of said tube into an interior cavity or a passageway is immediately prior to said step of temporarily inserting said sensor probe within said probe-receiving tube.

30. The method of claim 27 wherein said step of temporarily inserting said sensor probe within said probe-receiving tube is prior to said step of inserting said distal portion of said support member together with said closed distal end of said tube into an interior cavity or a passageway.

31. The method of claim 27 wherein said step of temporarily inserting said sensor probe within said probe-receiving tube further comprises the step of temporarily inserting a non-sterile sensor probe within said probe-receiving tube.

32. A method for using a guidable biopsy needle, comprising:

(a) providing, within a guidable biopsy needle, a probe-receiving tube defined within said biopsy needle, said tube having a sensor permeable closed distal end defining an interior space within said tube suitable for receiving a sensor probe, said biopsy needle having a specimen notch for collecting a tissue sample;

(b) temporarily inserting a sensor probe within said probe-receiving tube and into proximity with said sensor permeable closed distal end thereof;

(c) inserting said biopsy needle, in a closed position with said specimen notch covered, into body tissue of a patient;

(d) using said sensor probe to guide said guidable biopsy needle to a desired location within said patient while said sensor probe is within said probe-receiving tube; and (e) using said biopsy needle, collecting said tissue sample within said specimen notch.

33. The method of claim 32 wherein said step of inserting said biopsy needle into body tissue of a patient is immediately prior to said step of temporarily inserting said sensor probe within said probe-receiving tube.

34. The method of claim 32 wherein said step of temporarily inserting said sensor probe within said probe-receiving tube is prior to said step of inserting said biopsy needle into body tissue of a patient.

35. The method of claim 32 wherein said step of temporarily inserting said sensor probe within said probe-receiving tube further comprises the step of temporarily inserting a non-sterile sensor probe within said probe-receiving tube.

36. A device for use in a surgical procedure within a patient's body, comprising:

(a) an elongate support member having a distal end portion and a proximal portion;

(b) a sterile temporary ground pacing wire interconnected with at least said distal portion of said elongate support member, said ground pacing wire being directly attachable to a first side of a heart; and (c) a sterile temporary signal pacing wire interconnected with at least said distal portion of said elongate support member, said signal pacing wire being directly attachable to a second side of said heart.

37. The device of claim 36 further comprising a probe-receiving tube longitudinally adjacent said elongate support member, said tube having a closed distal end defining an interior space within said tube for receiving a non-sterile sensor, said ground and signal pacing wires being positioned at least partially longitudinally between said probe-receiving tube and said elongate support member.

38. A device for use in a medical procedure for placing a sensor probe temporarily in a desired location in a patient's body, comprising:

(a) an elongate support member having a distal end portion and a proximal portion; and (b) a blood character sensor mounted on said distal end portion of said support member, said sensor being directly interconnectible with an interior blood vessel.

39. The device of claim 38 wherein said elongate support member is a chest drain tube.

40. The device of claim 38 wherein said elongate support member is a portion of a chest drain tube.

* * * * *